United States Patent
Lane et al.

(10) Patent No.: US 10,987,327 B2
(45) Date of Patent: Apr. 27, 2021

(54) METHOD FOR PREVENTING OR TREATING AUTISM SPECTRUM DISORDERS BY BENZOIC ACID SALT

(71) Applicants: EXCELSIOR PHARMATECH LABS, Taipei (TW); Ying-Tung Lee, Bandar Sungai Long (MY); Hsien-Yuan Lane, Taichung (TW)

(72) Inventors: Hsien-Yuan Lane, Taichung (TW); Pin-Chen Yang, Kaohsiung (TW)

(73) Assignees: EXCELSIOR PHARMATECH LABS, Taipei (TW); Lane Hsien-yuan, Taichung (TW)

( * ) Notice: Subject to any disclaimer, the term of this patent is extended or adjusted under 35 U.S.C. 154(b) by 0 days.

(21) Appl. No.: 16/488,532

(22) PCT Filed: Jan. 4, 2018

(86) PCT No.: PCT/MY2018/000001
§ 371 (c)(1),
(2) Date: Aug. 23, 2019

(87) PCT Pub. No.: WO2018/160055
PCT Pub. Date: Sep. 7, 2018

(65) Prior Publication Data
US 2020/0061005 A1 Feb. 27, 2020

Related U.S. Application Data

(60) Provisional application No. 62/466,749, filed on Mar. 3, 2017.

(51) Int. Cl.
*A61K 31/192* (2006.01)
*A61P 25/28* (2006.01)

(52) U.S. Cl.
CPC ............ *A61K 31/192* (2013.01); *A61P 25/28* (2018.01)

(58) Field of Classification Search
CPC .............................. A61K 31/192; A61P 25/28
USPC ........................................................ 514/568
See application file for complete search history.

(56) References Cited

U.S. PATENT DOCUMENTS 6,362,226 B2 *   3/2002   Phillips, III ........... A61K 31/19
                                                          514/289
2015/0265559 A1   9/2015   Lane et al.

FOREIGN PATENT DOCUMENTS

WO    2001041707 A2    6/2001
WO    2015147742 A1    10/2015

OTHER PUBLICATIONS

Görker, I., & Tüzün, U.; "Autistic-like findings associated with a urea cycle disorder in a 4-year-old girl;" Journal of Psychiatry & Neuroscience ; CMA Media Inc.; vol. 30; No. 2, 2005; pp. 133-135 (3 pages).
Lane H, Lin C, Green MF, et al; "Add-on Treatment of Benzoate for Schizophrenia: A Randomized, Double-blind, Placebo-Controlled Trial of d-Amino Acid Oxidase Inhibitor;" JAMA Psychiatry; American Medical Association; vol. 70; No. 12; Dec. 2013; pp. 1267-1275 (9 pages).
Lin, Chieh-Hsin et al; "Benzoate, a D-Amino Acid Oxidase Inhibitor, for the Treatment of Early-Phase Alzheimer Disease: A Randomized, Double-Blind, Placebo-Controlled Trial"; Biological Psychiatry, vol. 75, Issue 9, 2014, 678-685 (8 pages).
International Search Report issued in Application No. PCT/MY2018/000001, dated Mar. 29, 2018 (4 pages).
Written Opinion issued in Application No. PCT/MY2018/000001, dated Mar. 29, 2018 (4 pages).
Walsh, Christopher A., et al; "Autism and Brain Development;" Cell; vol. 135; Elsevier Inc.; Oct. 31, 2008; pp. 396-400 (5 pages).
Sasabe, Jumpei, et al.; "D-Amino acid oxidase controls motoneuron degeneration through D-serine;" PNAS; vol. 109; No. 2; Jan. 10, 2012; pp. 627-632 (6 pages).
Yang, Pinchen and Chen-Lin Chang; "Glutamate-Mediated Signaling and Autism Spectrum Disorders: Emerging Treatment Targets;" Current Pharmaceutical Design; Bentham Science Publishers; vol. 20; No. 00; 2014; p. 1-8 (8 pages).
Vanoni, Maria A., et al; "Limited Proteolysis and X-ray Crystallography Reveal the Origin of Substrate Specificity and of the Rate-Limiting Product Release during Oxidation of D-Amino Acids Catalyzed by Mammalian D-Amino Acid Oxidase;" Biochemistry; American Chemical Society; vol. 36; No. 19; 1997; pp. 5624-5632 (9 pages).

(Continued)

*Primary Examiner* — Kevin E Weddington
(74) *Attorney, Agent, or Firm* — Osha Bergman Watanabe & Burton LLP

(57) ABSTRACT

A method for preventing or treating an autism spectrum disorder in a subject in need thereof may include administering to the subject a composition containing a therapeutically effective amount of a benzoic acid salt and a pharmaceutically acceptable excipient thereof. The benzoic acid salt may be administered to the subject in an amount ranging from 100 mg/day to 2000 mg/day.

13 Claims, No Drawings

(56) References Cited

OTHER PUBLICATIONS

Fukui, Kiyoshi and Yoshihiro Miyake; "Molecular Cloning and Chromosomal Localization of a Human Gene Encoding D-Amino-acid Oxidase;" The Journal of Biological Chemistry; The American Society of Biochemistry and Molecular Biology, Inc.; vol. 267; No. 26; Sep. 15, 1992; pp. 18631-28638 (8 pages).

Lau, C. Geoffrey and R. Suzanne Zukin; "NMDA receptor trafficking in synaptic plasticity and neuropsychiatric disorders;" Nature Reviews: Neuroscience; Nature Publishing Group; vol. 8; Jun. 2007; pp. 413-427 (15 pages).

Spooren, Will, et al.; "Synapse dysfunction in autism: a molecular medicine approach to drug discovery in neurodevelopmental disorders;" Cell Press; Trends in Pharmacological Sciences; vol. 33; No. 12; Dec. 2012; pp. 669-684 (16 pages).

* cited by examiner

METHOD FOR PREVENTING OR TREATING AUTISM SPECTRUM DISORDERS BY BENZOIC ACID SALT

BACKGROUND

1. Technical Field

The present disclosure relates to a method for preventing or treating an autism spectrum disorder, and specifically to a method for preventing or treating an autism spectrum disorder by administering to a subject a composition comprising a benzoic acid salt. Also related is a composition for use in preventing or treating an autism spectrum disorder in a subject in need thereof.

2. Description of Associated Art

Current neuroscience researches hypothesized that autism spectrum disorders (ASDs) are neurodevelopmental disorders of the neuronal synapseses with abnormal connectivities (Spooren, Lindemann, Ghosh, & Santarelli, 2012: Walsh, Morrow, & Rubenstein, 2008). Molecules targeting brain dendritic spine regulation for the purpose of promoting its maturation and restoring spine stability are thus considered to be of therapeutic potential in ASDs. Because glutamate and its ionotropic N-methyl-D-aspartate (NMDA) receptors have been known to be associated with synaptic plasticity, glutamate and NMDA receptors-mediated signaling has become the target of interest in exploring the pharmacological treatment of ASDs (Lau & Zukin, 2007: Yang & Chang, 2014).

One possible approach is to raise synaptic concentrations of D-amino acids by reducing their metabolism by D-amino acid oxidase (DAAO) (Fukui & Miyake, 1992; Sasabe et al., 2012; Vanoni et al., 1997). Sodium benzoate is a readily available DAAO inhibitor with a well-developed safety profile. Benzoic acid and its salts are generally recognized as safe food preservatives and are widely used in manufacturing fruit jelly, butter, soybean sauce, and processed meat (US Food & Drag Administration 1972). In addition, sodium benzoate has been approved for the treatment of urea cycle enzymopathies, which is a rare disease usually diagnosed in childhood.

As for application of benzoate for neuropsychiatric disorders, two prior clinical trials have been reported. They were respectively a double-blind, placebo-controlled trial for an early-phase Alzheimer disease (Lin et al., 2014) and for schizophrenia (Lane et al., 2013). Significant improvements in clinical symptoms, neurocognitive ability and quality of life were observed in both clinical trials.

To test whether the benzoate is beneficial for ASDs, it has been conducted in the trials of the present disclosure to examine the efficacy and safety of sodium benzoate in patients with ASDs.

SUMMARY

On account of the supporting evidence, the present disclosure is provided that the benzoic acid salt could be beneficial for ASD due to its ability to indirectly augment the NMDA-mediated glutamertergic neurotransmission and thus may possibly enhance learning.

The present disclosure provides a method for preventing or treating an autism spectrum disorder in a subject in need thereof, comprising administering to the subject a composition comprising a benzoic acid salt and a pharmaceutically acceptable excipient thereof. Also provided is a composition for use in preventing or treating an autism spectrum disorder in a subject in need thereof.

In one embodiment of the present application, the benzoic acid salt may be sodium benzoate, potassium benzoate, calcium benzoate, 2-aminobenzoate, 3-aminobenzoate, or 4-aminobenzoate. In another embodiment of the present application, the benzoic acid salt may be sodium benzoate.

In one embodiment of the present disclosure, the autism spectrum disorder includes, but is not limited to, autism, Asperger's syndrome, childhood disintegrative disorder and pervasive developmental disorder.

In one embodiment of the present disclosure, the subject may be a child suffering from the autism spectrum disorder.

In one embodiment of the present disclosure, the subject may be of age from 2 to 12 years old, such as from 3 to 9 years old, and from 5 to 8 years old.

In one embodiment of the present application, the benzoic acid salt may be administered to the subject in an amount ranging from 100 mg/day to 2000 mg/day, such as from 150 mg/day to 1000 mg/day, from 200 mg/day to 750 mg/day, and from 250 mg/day to 500 mg/day.

In one embodiment of the present application, the composition may be administered to the subject in a period ranging from 2 months to 2 years, such as from 4 weeks to 12 months. In another embodiment of the present application, the composition is administered to the subject in a period of around 12 weeks.

Accordingly, the present disclosure provides a method to treat a subject affected with ASP. The method involves use of a benzoic acid salt and improves the communication skills of the subject, as observed in different assessment tests that measure language ability, vocabularies learned, level of development in seven domains including gross motor, fine motor, comprehension, expressive language, situation-comprehension, personal-social and self-help, as well as the assessment system for adaptive behaviors.

DETAILED DESCRIPTION OF THE EMBODIMENTS

The following examples are used to exemplify the present disclosure. A person of ordinary skill in the art can conceive the other advantages of the present disclosure, based on the specification of the present disclosure. The present disclosure can also be implemented or applied as described in different examples. It is possible to modify and/or alter the above examples for earning out this disclosure without contravening its spirit and scope, for different aspects and applications.

All terms including descriptive or technical terms which are used herein should be construed as having meanings that are obvious to one of ordinary skill in the art. However, the terms may have different meanings according to an intention of one of ordinary skill in the art, case precedents, or the appearance of new technologies. Also, some terms may be arbitrarily selected by the applicant, and in this case, the meaning of the selected terms will be described in detail in the detailed descriptions of the present disclosure. Thus, the terms used herein have to be defined based on the meaning of the terms together with the descriptions throughout the specification.

Also, when a part "includes" or "comprises" a component or a step, unless there is a particular description contrary thereto, the part can further include other components or other steps, not excluding the others.

It is further noted that, as used in this specification, live singular forms "a," "an," and "the" include plural referents unless expressly and unequivocally limited to one referent. The term "or" is used interchangeably with the term "and/or" unless the context clearly indicates otherwise.

The present disclosure provides a method for preventing or treating autism spectrum disorders in a subject, comprising administering to the subject a therapeutically effective amount of a benzoic acid salt, wherein the subject may be a subject suffering from an autism spectrum disorder.

As used herein, the term "autism spectrum disorder" refers to a single disorder that includes disorders of autism. Asperger's syndrome, childhood disintegrative disorder and pervasive developmental disorder.

As used herein, the term "spectrum" in autism spectrum disorders refers to a wide range of symptoms and severity.

As used herein, the term "treating" or "treatment" refers to administration of an effective amount of a benzoic acid salt to a subject in need thereof with the purpose of cure, alleviate, relieve, remedy, ameliorate, or prevent the disease, the symptoms thereof, or the predisposition towards it. Such a subject may be identified by a health care professional based on results from any suitable diagnostic method.

As used herein, the term "therapeutically effective amount" refers to the amount of a therapy that is sufficient to result in the prevention of the development, recurrence, or onset of an autism spectrum disorder and one or more symptoms thereof, to enhance or improve the prophylactic effect(s) of another therapy, reduce the severity, the duration of an autism spectrum disorder, ameliorate one or more symptoms of an autism spectrum disorder, prevent the advancement of an autism spectrum disorder, and/or enhance or improve the therapeutic effect(s) of another therapy.

In certain embodiments of the present disclosure, the method involves the use of the benzoic acid, benzoic acid salt, or derivatives thereof, which may be selected from the group consisting of benzoic acid, sodium benzoate, potassium benzoate, calcium benzoate, 2-aminobenzoate, 3-aminobenzoate, and 4-aminobenzoate.

In some embodiments of the present disclosure, the effective amount of the benzoic acid salt administered to the subject may range from 100 mg/day to 2000 mg/day. In an embodiment, a lower limit of the dosage may be 100 mg/day, 120 mg/day, 150 mg/day, 180 mg/day, 200 mg/day, 225 mg/day, 250 mg/day, 300 mg/day, 400 mg/day, or 500 mg/day, and an upper limit of the dosage may be 2000 mg/day, 1500 mg/day, 1200 mg/day, 1000 mg/day, 900 mg/day, 750 mg/day or 500 mg/day. For example, the dosage of the benzoic acid salt may be from 200 mg/day to 2000 mg/day, 250 mg/day to 1500 mg/day, 150 mg/day to 1000 mg/day, 500 mg/day to 1000 mg/day, 500 mg/day to 900 mg/day, 200 mg/day to 750 mg/day, 250 mg/day to 500 mg/day, around 500 mg/day, or around 250 mg/day.

In some embodiments of the present disclosure, the benzoic add salt administered to the subject is contained in a pharmaceutical composition. The pharmaceutical composition of the present disclosure comprises a benzoic acid salt and a pharmaceutically acceptable excipient thereof. In an embodiment, the composition of the present disclosure is formulated in a form suitable for oral administration, and thus the composition may be administered to the subject by oral delivery. Alternatively, the composition may be formulated in a form of dry powder, a tablet, a lozenge, a capsule, granule, or a pill. The pharmaceutically acceptable excipient includes, but is not limited to, a filler, a binder, a preservative, a disintegrating agent, a lubricant, a suspending agent, a wetting agent, a solvent, a surfactant, an acid, a flavoring agent, polyethylene glycol (PEG), alkylene glycol, sebacic acid, dimethyl sulfoxide, an alcohol, or any combination thereof.

In some embodiments of the present disclosure, the administration of the composition comprising a benzoic acid salt may be conducted, for example, once per day, twice per day, 3 times per day, or 4 times per day. In an embodiment, the administration of the composition comprising a benzoic acid salt may be conducted once per day.

In some embodiments of the present disclosure, the composition may be administered to the subject in a period sufficient to prevent or treat an autism spectrum disorder. The sufficient period may depend on the species, gender, body weight or age of the subject, the stage, symptom or severity of the disease, and the routes, timing or frequency of the administration. In some embodiments of the present disclosure, the administration of the composition is daily over at least one month. For example, the period of administration of the composition may last for 1, 2, 3, 4, or 6 months, or 1, 2, 3 or 4 years, or even longer, as long as no side effect occurs during the treatment period. In the exemplary embodiments of the present disclosure, the period may be in a range of from 2 months to 2 years. In another embodiment, the period ranges from 4 weeks to 12 months. In yet another embodiment, the administration of the benzoic acid salt is daily for 12 weeks.

In some embodiments of the present disclosure, the subject administrated with the benzoic acid salt is a child. In an embodiment, the age of the subject may be in a range of from 2 to 12 years old, such as front 3 to 9, from 3 to 5, from 4 to 6, or from 5 to 8 years old.

The pharmaceutical composition of the present disclosure may only comprise the benzoic acid salt as an active ingredient for preventing or treating an autism spectrum disorder. In other words, the benzoic acid salt serves as the only active ingredient for the autism spectrum disorder in the composition. In this embodiment, the present disclosure provides a safe and effective therapy for preventing or treating autism spectrum disorders by the use of the benzoic acid salt alone as the active ingredient.

Alternatively, in another embodiment, the composition may be administered to a subject in combination with another active ingredient unless the effect of the disclosure is inhibited, live benzoic acid salt and another active ingredient may be provided in a single composition or in separate compositions.

In an embodiment, the administration of the benzoic acid salt in the method provided by the present disclosure may be combined with any suitable conventional therapy for autism spectrum disorders.

Many examples have been used to illustrate the present disclosure. The examples below should not be taken as a limit to the scope of the present disclosure.

EXAMPLE

The present disclosure examined the efficacy and safety of sodium benzoate, a D-amino acid oxidase inhibitor, for the treatment of an autism spectrum disorder.

Six children with ASD were treated with 250 to 500 mg/day of sodium benzoate for 12 weeks. At the baseline and the final (12 weeks) visit, the assessments of receptive and expressive vocabulary test (REVT), core vocabularies gained in the core vocabulary communication system, Chinese child developmental inventory, adaptive behavior assessment system-II (ABAS-II), parenting stress index (PSI), clinical global impression-improvement scale (CGI-I) were arranged.

Participants

This study was a twelve-week open label trial with the aim of gaining experience with sodium benzoate for the treatment of non-communicative children with ASDs. The participants were a convenient sample of outpatients children recruited from the Department of Pediatrics, Kaohsiung Medical University Hospital, Taiwan.

All these children were already diagnosed as with an autistic disorder by DSM-IV (Association, 2000). Before entering this study, they all received careful reassessment using DSM-5 criteria to be ascertained of meeting the ASD criteria (American Psychiatric Association 2013). The other inclusion criteria for participation of this study were: (1) the child was currently with severe communication problem; (2) the child did not receive augmented picture exchange communication system for communication; and (3) parents could be cooperative with the at home training requirement. For children receiving other psychiatric medication, the drugs had to be at a stable dose for at least 2 months before entering the study and remained unaltered throughout the clinical trial. Concomitant educational, occupational, physical or behavioral treatment was permitted, but no new treatment was allowed to be added except the communication training provided in this trial. The research protocol was approved by the Institutional Review Boards (Registration No.: F(I)-20150003) of the hospital mentioned above.

Trial Design

Six children, including five boys and 1 girl with ages between 3-year-7-month to 9-year-10-month old, were assigned to receive a 12-week treatment of sodium benzoate. For children with a body weight equal or more than 15 kg, benzoate was given with 500 mg/day. For children with a body weight less than 15 kg, benzoate was given with 250 mg/day. Sodium benzoate was provided by Excelsior Pharmatech Labs (Taiwan).

All the children entering this study also started to receive communication training using the Core Vocabulary Communication System—Chinese version (the Unlimiter Assistive Technology Engineering Lab, Taiwan). Parents were required to teach their children 40 minutes per day at home using this System. During the 12-week period, the parents were required to bring children back the hospital every 2 weeks. At the baseline and the final (12 weeks) visit, the following assessments were arranged.

Assessments

1. Receptive and Expressive Vocabulary Test—Chinese (REVT)

REVT assesses the language ability of children between 3-year and 6-year-11-month of age, and also for children older than 7-year-old who have language developmental delay. The Chinese version of REVT with normative data has been available since 2011 (Hwang, 2011). The REVT-Chinese has two parts, i.e., the receptive part and expressive part. The test results are usually scores and presented as a norm-referenced standard score. However, our nonverbal participants were either not testable or completed at the floor score, and thus results are reported by two domains (i.e., receptive and expressive) in percentile achieved as compared with standardized norm.

2. Core vocabularies gained in the Core Vocabulary Communication System

There are total 72 core vocabularies depicted in pictures in the Chinese Core Vocabulary Communication System, and they are tested in two ways: (1) by asking the participant to identify the pictures through "point-to-the-picture-of-the-word-I-say" technique; and (2) by asking the participant to name the individual picture. Results were reported by the total vocabularies the child learned through the 12 weeks period.

3. The Chinese Child Developmental Inventory—Chinese version (CCDI)

The Chinese Child Developmental Inventory (CCDI-Chinese) (Chu, 2007; Ko et al., 2008) is a 320-item parent-report measure of development which targets seven domains, i.e., gross motor, fine motor, comprehension, expressive language, situation-comprehension, personal-social and self-help. An integrated domain called "General Development" was derived from the seven domains and was usually used as index for global development. Developmental Quotient (DQ) is calculated by the months obtained in General Development divided by chronological age×100. Results were reported by pre- and post-DQ.

4. The Adaptive Behavior Assessment System-II (ABAS-II)—Chinese Version

The ABAS-II is an individually administered, norm-referenced measure of adaptive behaviors (Harrison and Oakland, 2003). The parent provided information in the skill areas of communication, community use, functional academics, home living, health-safety, leisure, self-direction and social skills. A Global Adaptive Composite (GAC) score is calculated from all nine skill area scores and presented as a norm-referenced standard score. Results were recorded by the pre- and post-GAC score and Social score.

5. Parenting Stress Index—Chinese Version (PSI)

Primary caregiver filled out the Chinese version of the parenting stress index (Wen, 2003) which was a validated Chinese version of the original questionnaire developed by Abdin (Abidin, 1986) that measured aspects of parental functioning. The PSI parent domain scale contains 54 items, and the child domain scale contains 47 items. In addition to the thirteen subscales, the parent and child domains yield a total score and a derived raw-to-percentile score. As reported by the validated Chinese PSI manual, the "total stress score" used a cut-off score of 286 for the abnormal band (equivalent to derived raw-to-percentile score above 85 percentile) (Wen, 2003).

6. Children's Global Assessment Scale (CGAS)

The CGAS is aimed at children and young people under 18 years old and is completed by clinicians to give a single score between 1 and 100, based on the assessment of a range of aspects related to a child's psychological and social functioning. The score will put them in one of ten categories that range from 'extremely impaired' (1-10) to 'doing very well' (91-100).

7. Clinical Global Impression-Improvement Scale (CGI-I)

The CGI-I is an observer-rated scale that measures the global improvement of illness as compared to condition at admission to the trial (Guy, 1976). The improvement is measured using a range of responses from 1 through 7: (1) very much improved; (2) much improved; (3) minimally improved; (4) no change; (5) minimally worse; (6) much worse; and (7) very much worse.

Results

Child A was a boy diagnosed as with ASD when he was at 3-year-1-month of age. He had already received pivotal response training focusing on joint attention, individual speech therapy, behavioral training and motor training. At the time of the study entry, he was at 4-year-4-month-old and would say some names of different kinds of cars and bulldozes. He would point to the door indicating his wish to go out and pointed to numerical numbers while demanding parents to read them out loud. He little smiled and usually lied on the floor and pushed the car around by himself. After 12 weeks into the study, child A was considered to be much improved. At the final assessment day, he was with a smiling face, and uttered in short sentence spontaneously (e.g., saying "I do not want tea, I want water" while seeing the picture of tea). When we tested him by showing the picture of "eyes," he responded as "Eyes, I do not want the eye drop in my eyes" (referring to his experience of visiting ophthalmologist for eye infection). However, he was still not able to be engaged in reciprocal talk.

Child B was a 5-year-9-month-old girl with non-communicative speech when she entered the trial. She was diagnosed as with ASD when she was at 3-year-8-month of age. At the baseline, she would have repeated sentences with no meaning for the context and was not able to be engaged in reciprocal conversation. She was always in a happy mood, but would become irritable when her preferred daily routines were disrupted. During the study, child B had mastered all the core vocabularies, and gradually whispered some of the picture naming task. Her parents noticed obvious increase amount of her speech and her being more willing to accept prompt and correction. We concluded child B to be much improved in this clinical trial.

Child C was a 9-year-6-month-old boy with limited words when he entered the trial. He could say the name of several food items to indicate his need, but no other meaningful phrases could be expressed. He would keep repeating "twenty seconds, twenty seconds" to himself when he was alone. Child C was diagnosed as with ASD when he was at 2-year-6-month of age. Due to limited communicative ability, he was put in special class from grade 1. He also received psychiatric medication of methyphenidate and risperidol from the age of 6-year-9-month due to labile mood, irritability, restlessness and poor sleep, and the doses were unaltered since the age of 8-year-3-month. After entering the trial, the only obvious gain was for him to be familiar with the name of the days (e.g., Monday, Tuesday, Wednesday . . . ). At the final assessment day, the only answer he could reply promptly was to the question of "What day is today?" In addition, in the first 3 days of benzoate usage, he was not able to fall asleep at his usual sleep time, albeit the night time medication of risperidol usage was unaltered. Mother reported that he would stay awake in bed and mumbled incomprehensible sounds in a self-soothing way for one hour more. We concluded child C to be of minimal improvement.

Child D was a 3-year-7-month-old boy who was diagnosed as with ASD when he was at 1-year-8-month of age. He had received pivotal response training on joint attention. At the baseline, child D had no meaningful words and was with a high activity level. He kept running and sliding on the floor or climbing up and down. At the final assessment day, child D showed no improvement. He still had no meaningful word, and showed no interest in the training pictures, communication board and talking pen. He was quite happy all the time, and his activity level became even higher. Constant adult supervision was needed to keep him from danger due to excessive running. His sleep pattern was unaltered.

Child E was a 8-year-4-month-old boy who could only say simple phrases (e.g., "Eat cookie," or "wait a minute") under strong maternal insistence. He was diagnosed as with ASD when he was at 3-year-6-month of age. Due to limited communicative ability, he was put in special class from grade 1. After entering the trial, child E showed interest in using the talking touch pen and communication board from the very beginning. He became more willing to increase the length of his utterance by copying parental remark. The self-talking at home also increased. At the 56 days on the trial, he could say "Mother. I want to eat cookie." At the last visit (the 84$^{th}$ in trial), he could whisper "How are you, doctor?" under mother's prompt when we met and said "Bye-bye, doctor" spontaneously when he left. However, in the first two weeks of the trial, his activity level increased. His mother described him as "always rushed in and out, climbed up and down." The activity level gradually returned to the baseline one month later. His sleep pattern was unaltered. Child E was concluded as much improved.

Child F was a 4-year-1-month-old boy who was diagnosed as with ASD when he was at 1-year-6-month of age. At the baseline of this trial, he could only say the names of certain foods under strong maternal prompt. He would lie on the floor immersing in his own world by lining up toy cars, and totally ignored adult's bidding. At the end of the trial, he could point and name about one fourth of the Core Vocabularies in the Communication system, but he still had no use of them. However, he was noted to manifest change in his daily home activity by increasing observation of his younger brother at play. He was no longer intensely preoccupied with his monotonous car line-up play. We concluded child F to be minimally improved.

The results of above cases were summarized in Table I.

TABLE 1

Characteristics and outcome measures of the subjects

| | | A | B | C | D | E | F |
|---|---|---|---|---|---|---|---|
| Age | | 4Y4M | 5Y9M | 9Y6M | 3Y7M | 8Y7M | 4Y1M |
| Gender | | M | F | M | M | M | M |
| DQ | Pre-Tx | 56 | 39 | 24 | 42 | 31 | 45 |
| | Post-Tx | 79 | 42 | 25 | 46 | 35 | 44 |
| REVT-R % | Pre-Tx | <1% | <1% | <1% | x | x | x |
| | Post-Tx | 32% | <1% | <1% | x | <1% | x |
| REVT-E % | Pre-Tx | <1% | <1% | <1% | x | x | x |
| | Post-Tx | 24% | 3% | <1% | x | x | x |
| CV-I (total number) | Pre-Tx | 55 | 50 | 45 | x | 16 | 0 |
| | Post-Tx | 72# | 72# | 45 | x | 42 | 21 |
| CV-N (total number) | Pre-Tx | 42 | 49 | 31 | x | 4 | 0 |
| | Post-Tx | 72# | 72# | 37 | x | 46 | 18 |
| ABAS-GCS | Pre-Tx | 77 | 60 | 47 | 53 | 50 | 58 |
| | Post-Tx | 77 | 61 | 46 | 49 | 53 | 57 |
| ABAS-S | Pre-Tx | 71 | 51 | 57 | 61 | 46 | 45 |
| | Post-Tx | 77 | 51 | 50 | 44 | 46 | 45 |
| PSI % | Pre-Tx | 70 | 97.5* | 99* | 99* | 69 | 50 |
| | Post-Tx | 62 | 93* | 99* | 99.9* | 75 | 72 |

TABLE 1-continued

Characteristics and outcome measures of the subjects

|  |  | A | B | C | D | E | F |
|---|---|---|---|---|---|---|---|
| CGAS | Pre-Tx | 40 | 40 | 40 | 21 | 40 | 40 |
|  | Post-Tx | 60 | 51 | 40 | 21 | 50 | 40 |
| CGI |  | much | much | minimal | nil | much | minimal |

DQ: developmental quotient derived from the Chinese Child developmental inventory
X: not able to be tested
REVT-R: Receptive and Expressive Vocabulary Test-receptive part, results are reported in percentile achieved as compared with standardized norm
REVT-E: Receptive and Expressive Vocabulary Test-expressive part, results are reported in percentile achieved as compared with standardized norm
CV-I: core vocabularies the child can identity in the pictures of Communication System by pointing (maximal as 72, marked as #)
CV-N: core vocabularies the child can identity in the pictures of Communication System by pointing (maximal as 72, marked as #)
ABAS-GCS: Parental reported General Adaptive Composite Score from Adaptive Behavior Assessment System-II
ABAS-S: Parental reported Social Score from Adaptive Behavior Assessment System-II
PSI: parenting stress index, * is marked when the derived raw-to-percentile score is above 85 percentile
CGAS: Children's Global Assessment Scale
CGI: Clinical Global Impression-Improvement The results of this trial reveal that the benzoic acid salt has beneficial effects in teaching of communication skill as observed by the parents and clinicians. Half of the participants (child A, B, E) were judged to be much improved. It is also revealed that the benzoic acid salt has an untoward activating effect in further increasing the originally high activity level of two subjects (child D, E) and affecting sleep (child C). Nevertheless, the activity levels of these three children were not disturbed to the extent of requiring medical attention or withdrawal from the trial. Accordingly, the present disclosure provides that the benzoic acid salt such as sodium benzoate, a DAAO inhibitor, is beneficial for ADS.

The foregoing descriptions of the embodiments are only illustrated to disclose the principle and functions of the present disclosure and do not restrict the scope of the present disclosure. It should be understood to those skilled in the art that all modifications and variations according to the spirit and principle in the disclosure of the present disclosure should fall within the scope of the appended claims. It is intended that the specification and examples are considered as exemplary only, with a true scope of the disclosure being indicated by the following claims.

The references listed below in the application are each incorporated by reference as if they were incorporated individually.

Abidin, R. (1986). *Parenting Stress Index: Manual Odessu.* FL: Psychological Assessment Resources, Inc.

American Psychitric Association, (2000). *Diagnosis and statistical manual of mental disorders, 4th Edn. Text Revision.* Washington D.C.: American Psychiatric Association.

American Psychitric Association, (2013). *Diagnosis and statistical manual of mental disorders, 5th Edn.* Washington D.C.: American Psychiatric Association.

Chu, P. Y. (2007). *Diagnostic validity of Chinese Child Development Inventory in screening children with developmental delay.* Master, National Cheng Kung University, Tainan, Taiwan.

Fukui, K., & Miyake, Y. (1992). Molecular cloning and chromosomal localization of a human gene encoding D-amino-acid oxidase. *J Biol Chem.* 267(26), 18631-18638.

Harrison, P. L., & Oakland, T. (2003). *Adaptive behavior assessment system (2nd ed.).* San Antonio, Tex.: Harcourt Assessment, Inc.

Hwang, R. J. (2011). *Receptive and Expressive Vocabulary Test—Chinese.* Taipei, Taiwan: Psychological Publishing Co.

Ko, H. C., Chu, P. Y., Lu, W. M., Kao, C. C., Kung, I. S., Chiu, Y. W., & Hu, S. Y. (2008). Chinese Child Development Inventory: an updated normative data. *Psychological Testing,* 55(2), 313-340.

Lane, H. Y., Lin, C. H., Green, M. F., Hellemann, G., Huang, C. C., Chen, P. W., & Tsai, G. E. (2013). Add-on treatment of benzoate for schizophrenia: a randomized, double-blind, placebo-controlled trial of D-amino acid oxidase inhibitor. *JAMA Psychiatry,* 70(12), 1267-1275.

Lau, C. G., & Zukin, R. S. (2007). NMDA receptor trafficking in synaptic plasticity and neuropsychiatric disorders, *Nat Rev Neurosci,* 8(6), 413-426.

Lin, C. H., Chen, P. K., Chang, Y. C., Chuo, L. J., Chen, Y. S., Tsai, G. E., & Lane, H. Y. (2014). Benzoate, a D-amino acid oxidase inhibitor, for the treatment of early-phase Alzheimer disease: a randomized, double-blind, placebo-controlled trial. *Biol Psychiatry,* 75(9), 678-685.

Sasabe, J., Miyoshi, Y., Suzuki, M., Mita, M., Konno, R., Matsuoka, M., & Aiso, S. (2012). D-amino acid oxidase controls motoneuron degeneration through D-serine. *Proc Natl Acad Sci U.S.A.,* 109(2), 627-632.

Spooren, W., Lindemann, L., Ghosh, A., & Santarelli, L. (2012). Synapse dysfunction in autism: a molecular medicine approach to drug discovery in neurodevelopmental disorders. *Trends Pharmacol Sci,* 33(12), 669-684.

US Food & Drug Administration, (1972). *GRAS (Generally Recognized As Safe) Food Ingredients: Benzoic Acid and Sodium Benzoate.* Washington, D.C.: US Food and Drug Administration.

Vanoni, M. A., Cosma, A., Mazzeo, D., Mattevi, A., Todone, F., & Curti, B. (1997). Limited proteolysis and X-ray crystallography reveal the origin of substrate specificity and of the rate-limiting produce release during oxidation of D-amino acids catalyzed by mammalian D-amino acid oxidase, *Biochemistry,* 36(19), 5624-5632.

Walsh, C. A., Morrow, E. M., & Rubenstein, J. L. (2008). Autism and brain development, *Cell,* 135(3), 396-400.

Wen, B. (2003). *Parenting Stress Index.* Taipei: Psychological Publishing Co. Ltd.

Yang, P., & Chang, C. L. (2014). Glutamate-Mediated Signaling and Autism Spectrum Disorders: Emerging Treatment Targets, *Curr Pharm Des,* 20(32), 5186-5193.

What is claimed is:

1. A method for preventing or treating an autism spectrum disorder in a subject in need thereof, comprising administering to the subject in need thereof a composition comprising a benzoic acid salt and a pharmaceutically acceptable excipient thereof, wherein the benzoic acid salt is administered to the subject in an amount ranging from 100 mg/day to 2000 mg/day, and the autism spectrum disorder is chosen from autism, Asperger's syndrome, childhood disintegrative disorder or pervasive developmental disorder.

2. The method according to claim 1, wherein the benzoic acid salt is sodium benzoate, potassium benzoate, calcium benzoate, 2-aminobenzoate, 3-aminobenzoate, or 4-aminobenzoate.

3. The method according to claim 1, wherein the benzoic acid salt is sodium benzoate.

4. The method according to claim 1, wherein the subject is a child suffering from the autism spectrum disorder.

5. The method according to claim 4, wherein the subject is of age from 2 to 12 years old.

6. The method according to claim 4, wherein the subject is of age from 3 to 9 years old.

7. The method according to claim 4, wherein the subject is of age from 5 to 8 years old.

8. The method according to claim 1, wherein the benzoic acid salt is administered to the subject in an amount ranging from 150 mg/day to 1000 mg/day.

9. The method according to claim 1, wherein the benzoic acid salt is administered to the subject in an amount ranging from 200 mg/day to 750 mg/day.

10. The method according to claim 1, wherein the benzoic acid salt is administered to the subject in an amount ranging from 250 mg/day to 500 mg/day.

11. The method according to claim 1, which is administered to the subject in a period ranging from 2 months to 2 years.

12. The method according to claim 1, which is administered to the subject in a period ranging from 4 weeks to 12 months.

13. The method according to claim 1, which is administered to the subject in a period of around 12 weeks.

* * * * *